United States Patent [19]

van der Heiden et al.

[11] Patent Number: 5,224,937
[45] Date of Patent: Jul. 6, 1993

[54] CLOSED SYRINGE-FILLING SYSTEM

[75] Inventors: Johannes van der Heiden, Groningen; Hubertus E. Hilbrink, Hemmen, both of Netherlands

[73] Assignee: NPBI Nederlands Produktielaboratorium voor Bloedtransfusieapparatuur en Infusievloeistoffen B.V., Emmer-Compascuum, Netherlands

[21] Appl. No.: 719,728

[22] Filed: Jun. 21, 1991

[51] Int. Cl.⁵ ............................................... A61M 5/24
[52] U.S. Cl. ................................. 604/200; 604/207; 604/190; 604/236; 604/905; 604/87
[58] Field of Search ............... 604/111, 190, 199, 200, 604/207, 236, 238, 239, 242, 244, 245, 272, 275, 256, 201, 202, 905, 82, 187, 88, 218, 89

[56] References Cited

U.S. PATENT DOCUMENTS

| | | | |
|---|---|---|---|
| 2,551,339 | 5/1951 | Ryan et al. | 604/232 X |
| 2,771,071 | 11/1956 | Mann | 604/215 |
| 2,869,544 | 1/1959 | Ratcliff et al. | 604/89 |
| 2,923,296 | 2/1960 | Adams et al. | 604/215 X |
| 3,010,705 | 11/1961 | Brown | 604/82 X |
| 3,275,509 | 9/1966 | Rowan et al. | 604/215 X |
| 3,307,552 | 3/1967 | Strawn | 604/256 |
| 3,581,743 | 6/1971 | Stein et al. | 604/111 |
| 3,978,859 | 9/1976 | Goodenough et al. | 604/111 X |
| 4,232,670 | 11/1980 | Richter et al. | 604/241 X |
| 4,300,678 | 11/1981 | Gyure et al. | 206/344 |
| 4,390,104 | 6/1983 | Cummings | 215/232 |
| 4,405,308 | 9/1983 | Jessup | 604/200 |
| 4,619,642 | 10/1986 | Spencer | 604/29 |
| 4,654,026 | 3/1987 | Underwood | 604/80 |
| 4,723,945 | 2/1988 | Thieling | 604/232 |
| 4,737,214 | 4/1988 | Leurink et al. | 156/158 |
| 4,795,429 | 1/1989 | Feldstein | 604/80 |
| 4,795,443 | 1/1989 | Permenter et al. | 604/198 |
| 4,834,706 | 5/1989 | Beck et al. | 604/111 |
| 4,899,903 | 2/1990 | Miyasaka et al. | 220/266 |
| 4,926,915 | 5/1990 | Deussen et al. | 141/290 |
| 5,009,645 | 4/1991 | Silver et al. | 604/207 |

FOREIGN PATENT DOCUMENTS

| | | | |
|---|---|---|---|
| 44204 | 4/1942 | Switzerland | 604/200 |
| 428093 | 7/1967 | Switzerland | 604/87 |

OTHER PUBLICATIONS

Sherwood Medical Catalog, Jul., 1990.

*Primary Examiner*—C. Fred Rosenbaum
*Assistant Examiner*—Mark O. Polutta
*Attorney, Agent, or Firm*—Herbert Dubno; Andrew Wilford

[57] ABSTRACT

A syringe assembly having a syringe has an outlet opening and a tube having an inner end hermetically sealed over the outlet opening and an outer end. Thus any contents of the syringe can flow unimpeded via the outlet into the tube and vice versa. A seal hermetically closes the outer end of the tube. Such a syringe assembly is filled from a medical-liquid-holding container also having an outlet opening provided with a respective such tube whose outer end is similarly sealed. The syringe is filled by first unsealing and joining the outer ends of the tubes to each other in a sterile docking procedure, then aspirating the medicament through the unsealed and joined ends and resealing the tubes together, and finally cutting the tubes apart where they are sealed together to form two new seals on the tube outer ends.

13 Claims, 5 Drawing Sheets

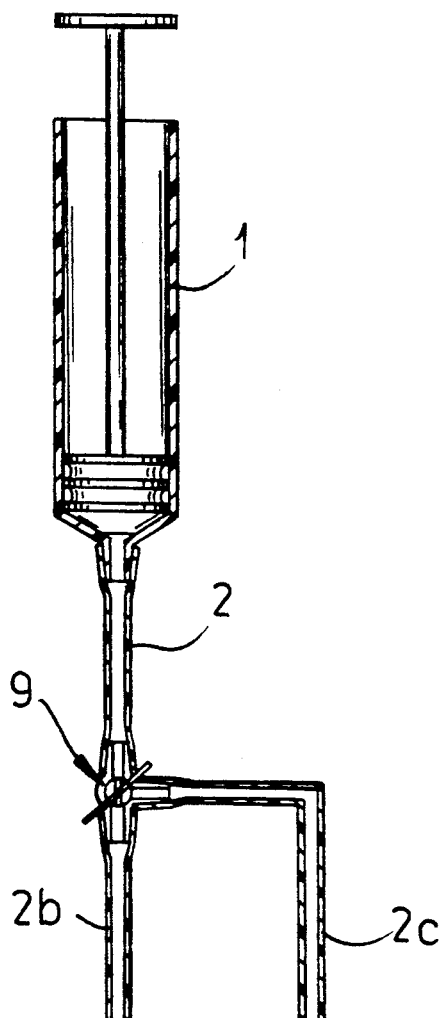
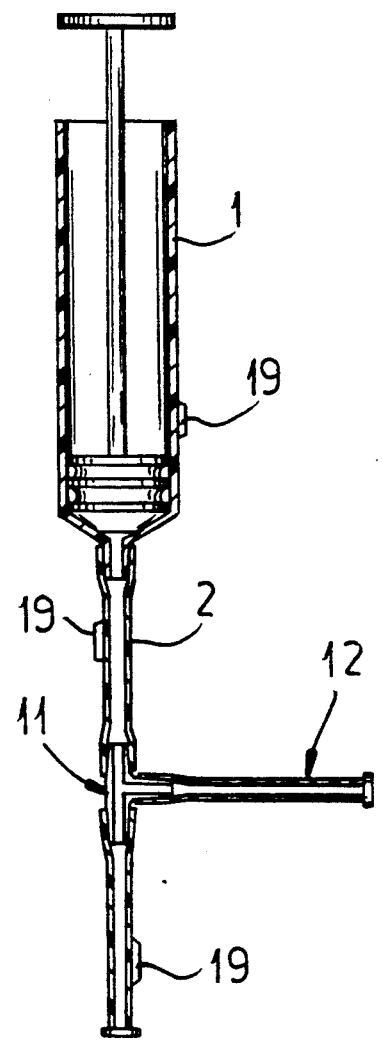
FIG.7
FIG.8

CLOSED SYRINGE-FILLING SYSTEM

FIELD OF THE INVENTION

The present invention relates to a method of and apparatus for filling a syringe. More particularly this invention concerns a closed system for filling a syringe.

BACKGROUND OF THE INVENTION

Syringes are widely used in the medical field for the administration of sterile fluids. The fluids administered to patients by means of a syringe may be plain physiological solutions such as physiological saline and dextrose 5% to compensate for fluid losses, they may contain a medicament to treat a disease, they may be a blood product to compensate for the shortage or loss of a blood component, or they may contain nutrients. These fluids may be administered with a syringe by direct intravenous (IV) push injection or as an infusion. Generally, if the fluid must by administered slowly in more than 5 min to 10 min, it is referred to as an infusion. For that purpose, special pumps are available that can accommodate a syringe.

Syringes are commercially available in sizes ranging from smaller than 1 ml to over 50 ml from many different manufacturers. Syringes of approximately 1 ml may be intended for specific purposes such as the administration of, for example, insulin or tuberculin and may have an integral needle. Syringes have a plunger with a piston that may be made of natural or silicone rubber slidable in a body or barrel and lubricated with a lubricant such as polydimethylsiloxane. The barrel is usually manufactured from a plastic such as polypropylene, polystyrene, or styrene/acrylonitrile copolymer. The barrel is provided with graduation lines and with a nozzle. The nozzle usually constitutes a male luer or luer-lock connector and may be fitted with a nozzle or tip cap to guard against accidental contamination. After packaging, this syringe is sterilized, usually by ETO-gas or by gamma or beta radiation and is supplied ready for one-time use.

The requirements that syringes must meet are described in many standards, especially ISO. ISO sets standards for the materials of the syringe, the manufacture, accuracy, performance etc. Also, ISO and other organizations set standards for the male luer or luer-lock connector that is provided on the syringe. ISO also sets standards for female luer connectors, thereby guaranteeing a leaktight fit of the connector on the syringe with any device with a female luer connector.

The state of the art in administering a sterile fluid in a syringe to a patient is to first fill the syringe with the solution to be administered. This solution may be held in a container made of a rigid material such as glass, of a semi-rigid material such as polyethylene or polypropylene, or of a flexible material such as polyvinylchloride. These containers usually have a port with a rubber septum or membrane that can be punctured with a needle to introduce in or withdraw fluid from the container.

To maintain the sterility of both the solution to be taken or sampled and the solution in the syringe, transfer is preferably performed under aseptic conditions in a LAF-cabinet by personnel trained in aseptic techniques and wearing special clothing. First, a needle is placed on the syringe. Needles usually have a female luer connector and therefore can be connected to the male connector of the syringe. Then, with the needle, the rubber membrane of the container is punctured. By applying force to the plunger, the required volume of solution is drawn into the syringe. Air is then expelled from the syringe. Subsequently, the needle is withdrawn from the container and the fluid may be administered to the patient immediately if preparation takes place at the bedside, or, after removal of the needle, a cap may be put on the nozzle of the syringe. After capping, the syringe may be labelled and packaged and sent to the ward for administration to the patient.

If the solution is intended for direct intravenous push injection, after removal and disposal of the cap, a needle is placed on the nozzle again, and the solution may be injected into a vein or may be injected into a running administration system. If the solution is intended for slow administration over more than 5 min it usually is administered with the aid of a syringe pump. For that purpose, the cap is removed from the syringe and disposed of and the nozzle is connected to a tube with a female luer connector. The tube is connected to the administration system of the patient with a needle via an injection port or a gum rubber injection site. For slow administration of sterile fluids in a volume up to 50 ml, the use of a syringe with a syringe pump is often preferred for reasons of accuracy, reliability, ease of use, and the presence of alarms on the pumps.

Although the use of a syringe may be the preferred way for the administration of small volumes of up to 50 ml of medical fluids to patients, it has some serious drawbacks. The main drawback results from the fact that the syringe must be filled in an open system, that is with the aid of a needle in an aseptic procedure. In an open, aseptic procedure, foreign material may be introduced into the fluid in the syringe as well as in the fluid in the container. Also, in such a procedure, there is a high incidence of leakage and spillage due to needle drips and aerosols.

During filling, micro-organisms may accidentally be introduced into the syringe or into the container from which the syringe is being filled. For that reason, sterile fluids that have been sampled, in this case both the fluid in the syringe and the fluid in the container from which the syringe was filled, usually are regarded as contaminated and have a limited shelf life. Depending upon the nature of the product, the storage conditions and the policy of the hospital, the stability period for both the fluid in the syringe and the fluid in the container is limited to 1 day to 7 days.

However, this limited shelf life itself does not preclude the microbiological contamination of the fluid in the syringe no of the fluid in the container that is being sampled. Another drawback of the method of filling a syringe is that a needle is required for the procedure. Use of a needle frequently leads to needle sticks. Also, the needle may accidentally cut through the wall of the IV container and the needle may lead to coring or laceration of the rubber membrane of the IV container and thus to particulate contamination of the IV fluid. Finally, the use of a needle requires considerable force to fill the syringe, as the needle presents a substantial restriction in the system. The use of a needle, and thus an open system, may also lead to contamination of the environment with the product that is being filled in the syringe. This contamination may occur through needle drips, aerosols that are formed, spillage and leakage.

The problems that result from the use of a needle in an open, aseptic system to fill the syringe will be illustrated with three examples illustrating the consequences of contamination of the fluid in the syringe, contamination of the fluid in the container and contamination of the environment with the fluid.

EXAMPLE 1

Contamination of the fluid in the syringe

Generally, a considerable number of patients in hospitals acquire an infection. Syringes that were contaminated during filling contribute to this phenomenon. As the room temperature in hospitals is generally high, many commonly used fluids may facilitate the growth of microorganisms (e.g. parenteral nutrition and dextrose injections), and administration may take place over a number of hours, these solutions in syringes may become heavily contaminated during use.

EXAMPLE 2

Contamination of the fluid in the container

Some neonates need blood or blood products immediately after birth. These must be administered slowly and in small volume and therefore administration via a syringe and a pump is the preferred method of administration. For that purpose, blood is drawn into the syringe from a standard donation. After transfer for microbiological reasons the storage period of blood products is restricted to 24 hrs. Thus, the original donation is discarded after 24 hrs. Therefore, if the child needs another transfusion on one or more of the next days, the blood must be taken from another donation.

As the average child in this situation needs approximately seven transfusions, this means that this child will be exposed to the blood of seven different donors. The higher the donor-exposure however, the higher is the chance of the transmission of virus's like HIV, CMV and hepatitis, and of the occurrence of transfusion reactions which may consist of fever, chills, hypersensitivity reactions etc. Also, the use of the blood of seven different donors means that, compatibility testing needs to be performed seven times, once for each new donation.

Thus the limited shelf life of a product that is used in an open system may itself be the cause of a new, medically undesirable situation for a patient. If, however, the original blood donation could be sampled with a sterile technique in a closed system, this single unit of blood could be used for all the transfusions the infant would need. This would reduce donor-exposure to a single instance and would greatly reduce the chances of transfusion reactions and the transmission of a virus. At the same time, use of such a technique could prevent microbial contamination of the transfusion product in the syringe as was discussed in Example 1 and could thus reduce the generally very high infection rate with these patients.

EXAMPLE 3

Contamination of the environment

Many cytotoxic drugs are preferably administered with the aid of a syringe and a syringe pump. For that purpose, first the syringe must be filled with the drug solution. As most of these cytotoxic drugs are themselves carcinogenic and therefore hazardous, the reconstitution and dilution of these substances is usually performed under strict procedures based upon, for example, the guidelines issued by the American Society of Hospital Pharmacists or based upon local rules and regulations. These usually comprise working in a special cabinet with filtered air, wearing special protective clothing, and observing special rules for handling the product and the waste that is generated during reconstitution.

The drug may either be in a liquid form or in a powdered form and may be contained within an ampoule or within a glass vial with a rubber stopper. If the drug is in a powdered form, first it must be reconstituted. After reconstitution, the dissolved drug is generally diluted in an IV container. After dilution, the solution needs to be transferred to the syringe from which it will be administered. A needle is put on the syringe and the required volume of the solution is drawn into the syringe. After withdrawal of the needle from the container, the needle is removed from the syringe. The luer connector on the syringe may be capped. For administration, the cap is removed and the syringe is placed in a pump and is connected to the IV administration system of the patient.

The use of this method of working is associated with a considerable chance of leakage, drips, etc. In particular the use of the needle during preparation and the removal of the protective cap carry the risk of inadvertent exposure to these hazardous, cytotoxic drugs.

Several techniques have been described that are able to provide open fluid communication in a closed system. These techniques are often referred to as sterile docking. Such techniques may employ special connectors such as described in U.S. Pat. Nos. 4,157,723 and 4,611,643. Most of these sterile docking techniques, however, make use of a simple piece of sealable tubing that is closed on one end and is in communication with a component on the other end. This tubing may be of a material such as PVC. The components that need to be coupled must both be fitted with such a piece of tubing. These tubes are put in an apparatus and are docked, that is unsealed and then sealed together. Such systems are described U.S. Pat. Nos. 4,369,799, 4,619,642, and 4,737,214. Such an apparatus for making sterile connections is marketed in the U.S. by the Haemonetics company. In addition a system to use sterile docking to connect a bag containing a sterile CAPD fluid to the intraperitoneal catheter of a patient is marketed in Europe by the Gambro company. Finally sterile docking is used in some blood banks for the production of blood components. For this purpose, sterile fluids in flexible containers with a PVC tube for sterile docking ar marketed in the Netherlands by NPBI.

OBJECTS OF THE INVENTION

It is therefore an object of the present invention to provide an improved method of and apparatus for filling a hypodermic syringe.

Another object is the provision of such an improved method of and apparatus for filling a hypodermic syringe which overcomes the above-given disadvantages, that is which uses a closed system avoiding the use of a needle.

SUMMARY OF THE INVENTION

The instant invention is a syringe assembly having a syringe having an outlet opening and a tube having an inner end hermetically sealed over the outlet opening and an outer end. Thus any contents of the syringe can flow unimpeded via the outlet into the tube and vice versa. According to the invention a seal hermetically closes the outer end of the tube. Such a syringe assembly is used with a container also having an outlet opening provided with a respective such tube whose outer end is similarly sealed. The method therefore comprises the steps of first unsealing and joining the outer ends of the tubes to each other in a sterile docking procedure, then aspirating the medicament through the unsealed and joined ends and resealing the tube together, and finally cutting the tubes apart where they are sealed together to form two new seals on the tube outer ends.

The outlet and inner end can be formed as a luer connection having tamper-indicating means. The tube and the inner end can also be unitary in a disposable system.

It is also within the scope of this invention to provide a filter in the tube intermediate the ends thereof and/or a clamp on the tube intermediate the ends thereof actuatable to restrict flow through the tube, and/or a check valve in the tube oriented to prevent flow away from the syringe.

In accordance with a further feature of this invention a three-port valve is provided in the tube having a lateral connection and a second tube independent of the first-mentioned tube is connected to the lateral connection of the valve. A flexible container can be connected to the second tube. A tee can be used instead of this three-port valve and its outer end can be provided with another seal for sterile docking or a medical-liquid bag.

It is also within the scope of this invention to provide a plurality of such syringes connected by respective inner tubes to inlets of a one-piece manifold having an outlet connected to a second tube whose outer end is sealed. Thus a plurality of syringes, for example for successive transfusions of a neonate, can be filled at one time from a single blood bag. In any circumstance the apparatus is packaged and sterilized by means of gas or radiation.

BRIEF DESCRIPTION OF THE DRAWING

The above and other objects, features, and advantages will become more readily apparent from the following, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing:

FIGS. 2 through 8 are views like FIG. 1 of further embodiments of this invention;

DETAILED DESCRIPTION

Figure 1:
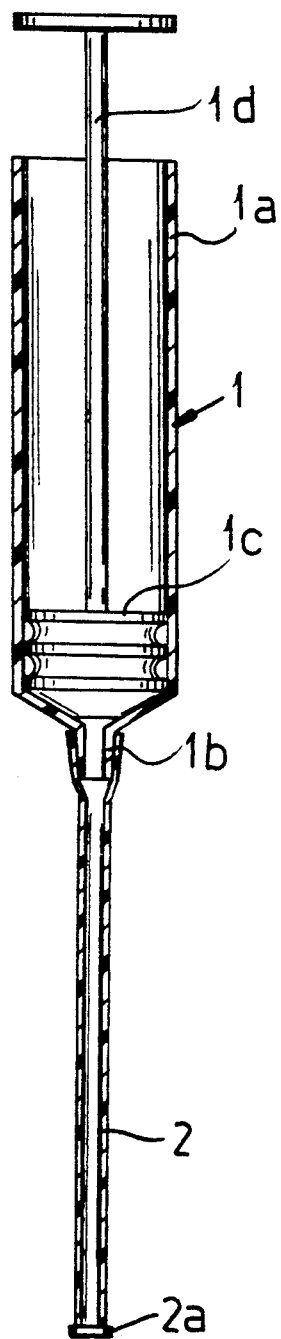
FIG. 1 is an axial section through a syringe according to this invention.

As seen in FIG. 1 a syringe 1 has a cylindrically tubular body 1a formed unitarily with an outlet nipple 1b and is provided internally with a piston 1c connected to a plunger 1d. The outlet nipple 1b is connected to the inner end of a sealable tube 2 having an outer end provided with a seal 2a that hermetically closes it. The tube can be attached via welding, gluing or clamping. For that purpose, the nozzle 1b of the syringe can be fitted with a hose coupling. The sealable tube 2 may then be fitted with a sleeve to prevent disconnection of the tube 2 due to high pressures such as may be generated by some syringe pumps. Apart from the nozzle 1b, the syringe may be of any known design and/or material and should preferably comply with all the other ISO specifications. The tube 2 can be made of a flexible, sealable material like e.g. PVC or polyethylene.

Figure 2:
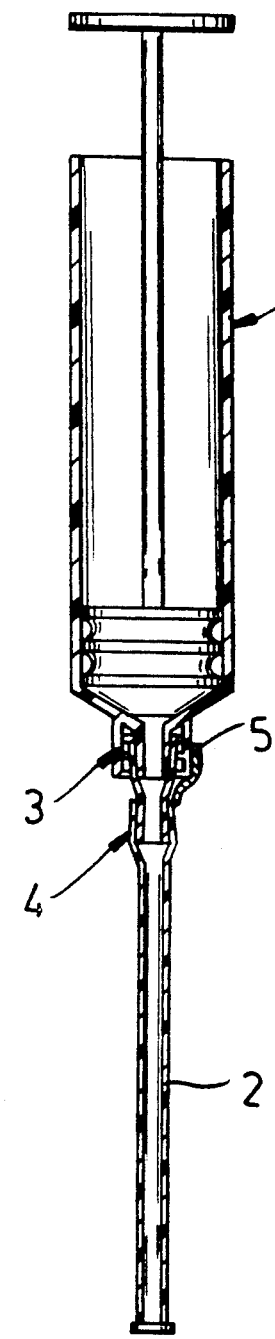

FIG. 2 shows a syringe according to ISO standards but where the closed, sealable tube 2 is connected to the male luer lock connector 3 of the syringe 1 via a female luer lock connector 4 on the tube. This connection may be equipped with a tamper evidence patch 5 for reasons of proof of sterility. This tamper evidence may also be a seal, or a piece of shrink-foil around the connectors or a breakable catch.

Figure 3:
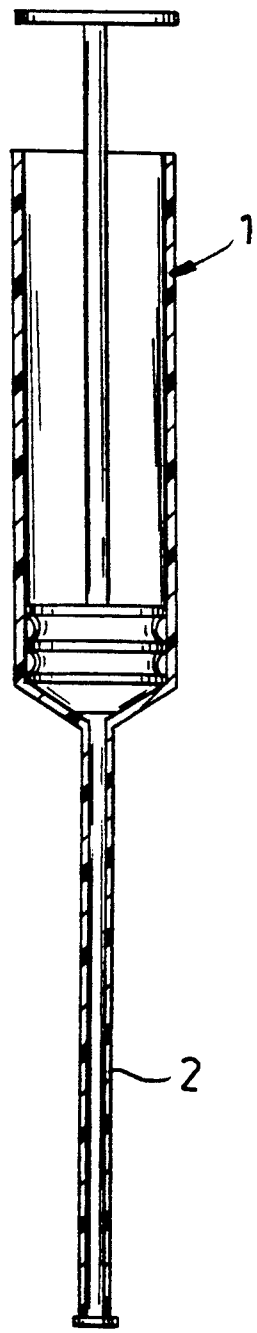

FIG. 3 shows a syringe 1 with an integral tube 2, that is the syringe 1 and the tube 2 are both made in one piece. They may be made from materials like polyethylene.

Figure 4:
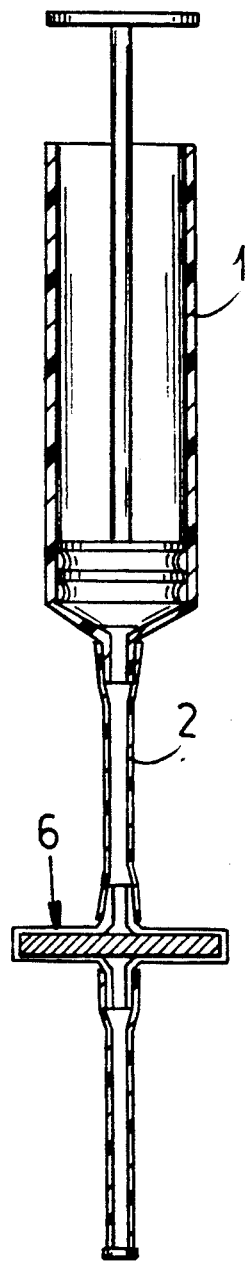

FIG. 4 shows a tube 2 fitted with a filter 6 for the removal of micro-organisms or particles from the fluid with which the syringe is filled. Generally, a filter with a pore size of 0.2 $\mu$m or larger is chosen for this purpose.

Figure 5:
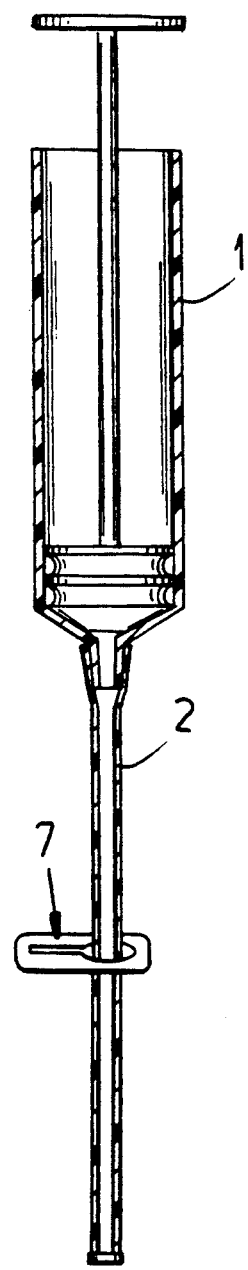

FIG. 5 shows a tube 2 fitted with a clamp 7. This clamp 7 may be used to temporarily shut off the flow of fluid through the tube 2.

Figure 6:
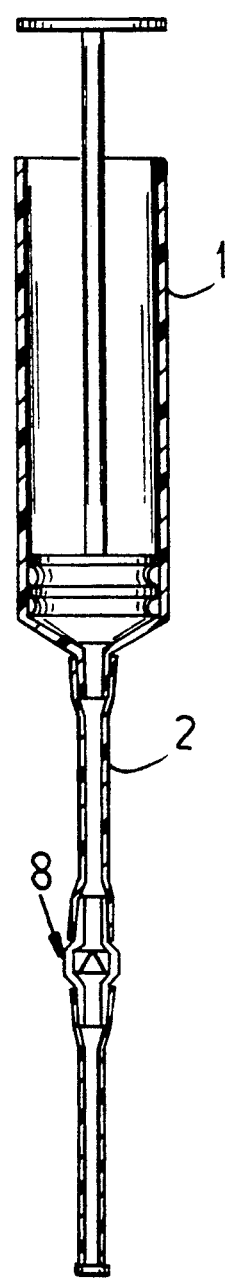

FIG. 6 shows a tube 2 fitted with a one-wa or check valve 8 allowing fluid flow only into the syringe. Such a valve will prevent contamination of the fluid in the container with a product that is contained in the syringe. Such a valve might be used if different fluids from more than one container must be sampled in the same syringe to prevent accidental mixing of the solution in the second container that is being sampled. Of course when the syringe 1 is to be used, the valve 8 is cut off.

FIG. 7 shows a tube 2 fitted with a three-port valve 9 having a lateral connection with an empty container 10. This valve 9 may allow communication between the syringe 1 and either of two pieces 2b and 2c of closed sealable tube. The tube 2b can be used to connect with the solution to be aspirated via sterile docking. After transfer, by turning the plug of the valve 9, open fluid communication is accomplished between the syringe 1 and the other tube 2c. To this other tube 2c a component can be coupled with the aid of sterile docking.

For instance, a flexible container 10, as shown in FIG. 7, may be connected to this tube 2c. Then, this container can be used as for example a waste bag to collect the air that is expelled from the syringe 1. Use of this three-port valve in this configuration therefore makes it possible to expel the air from the syringe in a closed system. This may be especially important in the preparation of cytotoxic drugs to prevent aerosols and spillage. It may also be important to keep the container that is being sampled essentially free of air, which may be important if the container that is being sampled contains a blood product or if the fluid is easily oxidized. Also, such a bag 10 may serve as a transfer bag or as a mixing bag to collect several portions of fluid which need subsequent mixing. However, any other component containing a sealable tube can be coupled to this valve 9.

FIG. 8 shows a tube fitted with a wye or tee 11 and a second closed sealable tube 12. This tube 12 can be used for the connection of other components with the aid of sterile docking. It may be connected to a flexible container that can serve as a transfer bag, as a waste bag, or as a mixing bag as described above.

Figure 9:
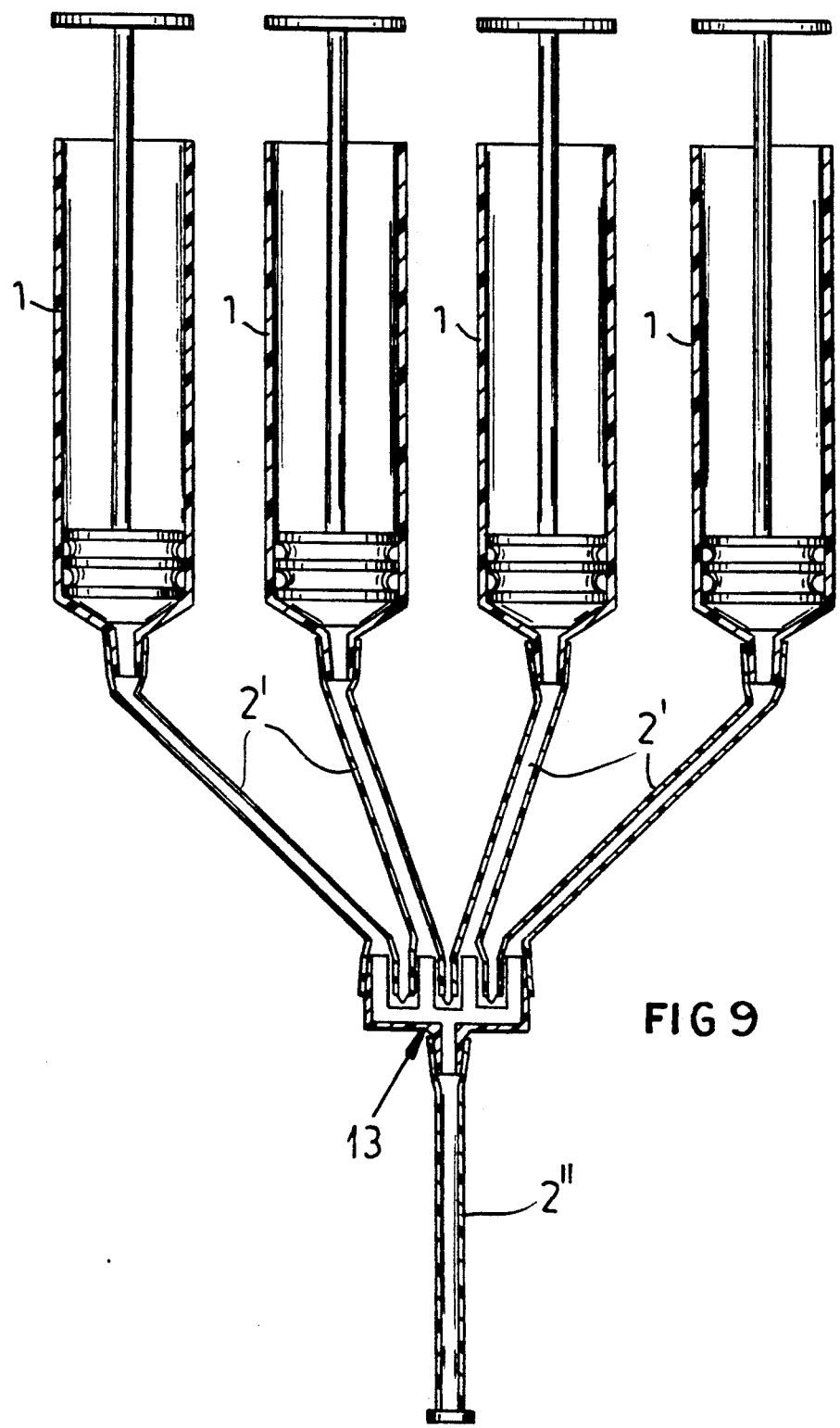
FIG. 9 is a view like FIG. 1 of a multiple syringe system.

FIG. 9 shows four syringes 1 having respective first tubes 2' connected to a manifold 13. One such manifold might for example connect four to 10 such syringes. After sterile docking of a single outlet tube 2" from the manifold 13 to a bulk container with a medical solution, these syringes 1 are filled, sealed and stored until use. This method of filling of syringes may be used in the preparation of parenteral nutrition for neonates in which usually at least one liter of solution must be compounded from which approx. twenty syringes can be filled at the same time. After filling, these syringes can be disconnected, sealed and can be stored until needed.

In any embodiment as seen in FIG. 8 the tube 2 and the syringe 1 may be fitted with some form of identification 19. For instance, the syringe and the tube may be fitted with labels or flag-labels or may be printed with a unique code. The tube 2 may be fitted with a number of identical identification-code labels 19 and the syringe, if the syringe and the tube can be disconnected may be fitted with at least one code with which the syringe and the tube can be matched. Identification codes consisting of numbers are in use on the tubes of standard blood bags to allow for a positive identification of the bag and samples taken from it. If a part of the tube of the syringe is taken as a sample for testing, positive identification with the syringe from which the sample was taken is possible. Also, after filling of the syringe from the container, a piece of tube with such an identification code can be left on the tube of the container for a positive match of the container and the syringe with the medical fluid. This may especially be important for the administration of blood products which are filled from a container and subsequently tested for compatibility with the patient's blood. Use of a positive means of identification may prevent an accidental break in administrative procedures and thereby increase the safety of blood transfusion. Also, for the administration of drug solutions, filled from a bulk-container, such identification codes might improve safety.

Any combination of the above mentioned embodiments forms part of this invention.

Figure 10A:
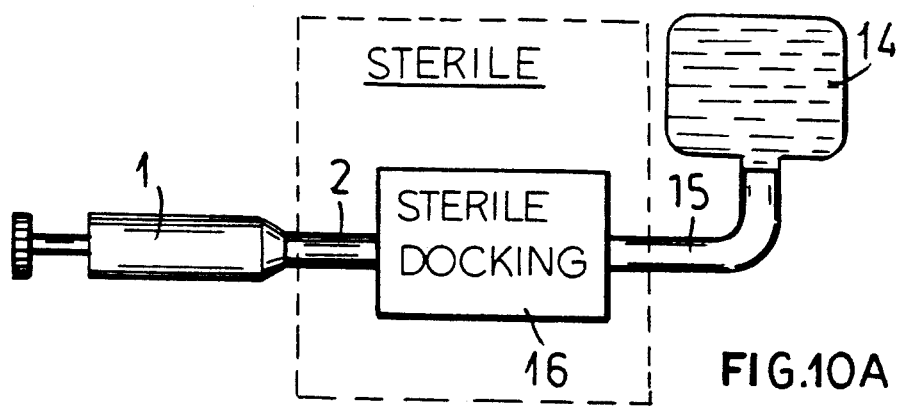
FIGS. 10A through 10D are largely schematic views illustrating the method of this invention.
Figure 10B:
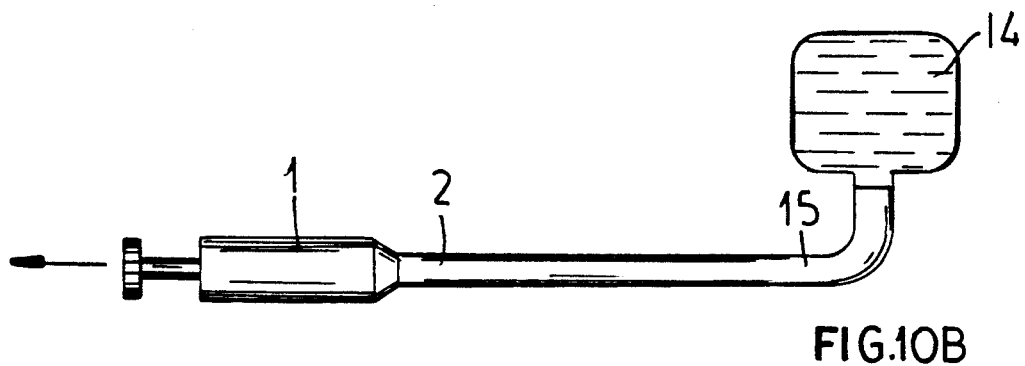
Figure 10C:
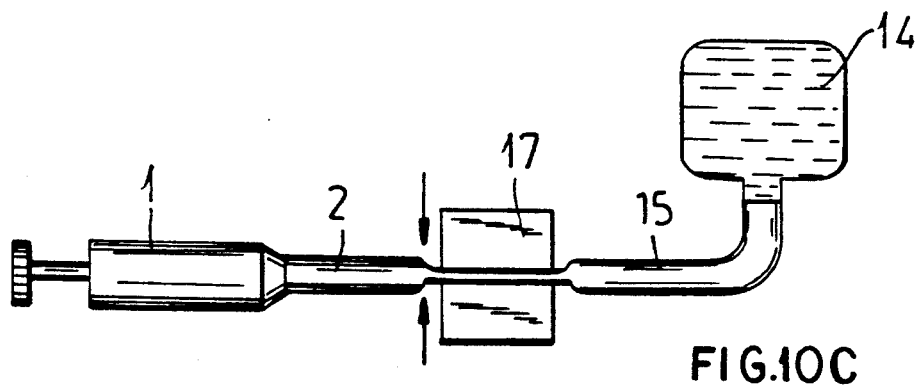

As seen in FIGS. 10A through 10D the method of this invention comprises the steps of first joining the tube 2 of a sterile, empty syringe 1 with a sealed tube 15 of a container 14 of the bag type shown at 10 in FIG. 7 filled with a medical fluid in a sterile-docking unit 16 as described in the above-mentioned patents. The container 14 can hold a standard IV solution, a diluted solution of a drug, or be a blood product. The tube 2 on the syringe and the tube 15 on the container may e.g. be made of a material like PVC or an other polymer that can be sealed. The sealable tubes 2 and 15 are put in the apparatus 16 for sterile docking where they are docked and joined together, thereby creating fluid communication between the container with the medical fluid and the syringe. The fluid is drawn into the syringe as shown in FIG. 10B. Air is expelled from the syringe and the syringe is filled with the exact amount of fluid required. Then as shown in FIG. 10C the tubes 2 and 15 are sealed in a unit 17. There are several methods for sealing tubes such as heat-sealing or RF-welding. An apparatus for sealing tubes is marketed in the U.S. by the Sebra company. Several patents describe these sealing techniques such as U.S. Pat. Nos. 4,013,860, 4,186,292, and 4,390,832

Figure 10D:
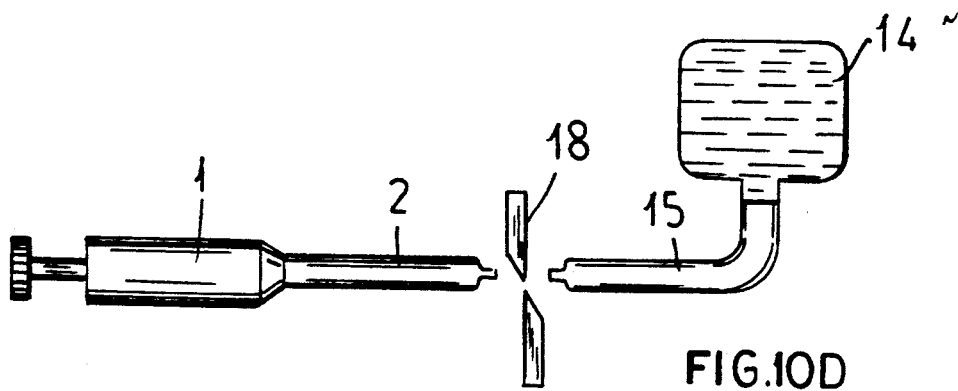

Then as shown in FIG. 10D the seal is severed by a cutter 18 or pulled apart at a preformed tear line to produce a syringe 1 with a medical fluid and a closed tube 2 and a container 14 with a closed tube 15. The tube 15 on the container can be used again to fill other syringes with the medical solution from the container. The syringe may then be labelled and transported to the ward as in the usual procedure.

If the fluid in the syringe must be administered to the patient via an administration system or needle with a female luer or luer lock, a luer-type syringe should be used. Before administration, the remaining sealable tube with the female luer connector should be removed, thus exposing the male luer connector on the syringe.

For direct IV push injection into a vein or into a running administration system, the syringe may then be coupled to the female luer connector of an injection needle and the fluid can be injected into the patient. For slow administration via a syringe pump, the connector of the syringe may be coupled to a female luer lock connector on an administration system or on a side-line which is connected to the administration system of the patient.

If the syringe need not be connected to an administration system of the patient by means of a female luer connector, either the embodiment in which the syringe has a direct connection with the tube or the embodiment in which the syringe and the tube are integrated in one piece, is preferably used. Via sterile docking, another tube can be connected to the tube 2 on the syringe. This tube may contain a break-away connector or a clamp and a connector for a needle. The needle can be pierced through an injection port of the patient's administration system. After placing the syringe in the pump and breaking the break-away connector, the fluid can be administered to the patient. This method of working is especially useful in the treatment of patients with cytotoxic drugs because it prevents the occurrence of aerosols and drips during connection of the syringe to the patient's administration system at the bed side.

Thus it is clear that the present invention offers many advantages over the prior art for filling a syringe in an open system. Use of a closed system prevents contamination of the solution in the syringe and of the solution in the container that is being transferred, and it prevents contamination of the environment with the product that is transferred. Furthermore, the disadvantages of working with needles are avoided.

Prevention of microbiological contamination of the solution in the syringe will increase the safety and may reduce hospital-acquired infection in patients. Also, this will increase the shelf life for a number of products, thus making recycling of unused doses possible. Prevention of microbiological contamination of the solution in the container that is sampled will increase the shelf life for these products, which is an advantage from an economic point of view. Furthermore, the increased shelf life also presents an advantage from a medical point of view as the same solution can be used more times for the same patient over a period of days or even weeks. This is especially important for patients who need small quantities of blood products to prevent transfusion-related reactions.

Prevention of contamination of the environment with the product that is transferred increases the safety of working with hazardous substances like cytotoxic drugs by reducing the chances of inadvertent exposure to these drugs due to aerosols, needle drips and the like. Furthermore, after transfer, both the syringe and the container that would contain a punctured rubber membrane in the prior art are again hermetically closed, sealed products.

Generally, the replacement of needles by a fluid path consisting of two tubes in fluid communication, offers a number of advantages. In the first place, needle sticks are prevented. In the second place, the container can not be punctured accidentally. In the third place, use of tubes is far more convenient as needles require considerably more force during injection and withdrawal of fluids. In the fourth place, as no rubber membrane needs to be punctured, no coring or laceration resulting in particles in the solution can take place.

We claim:

1. A syringe assembly comprising:
   a syringe having an outlet opening;
   a tube of a flexible and sealable thermoplastic synthetic resin and having an inner end hermetically fixed to the outlet opening and an outer end, whereby any contents of the syringe can flow unimpeded via the outlet into the tube and vice versa; and
   a seal unitary with and hermetically closing the outer end of the tube.

2. The syringe assembly defined in claim 1 wherein the outlet and the inner end are formed as a luer or luer-lock connection.

3. The syringe assembly defined in claim 1 wherein the tube and inner end are unitary.

4. The syringe assembly defined in claim 1, further comprising
   a filter in the tube intermediate the ends thereof.

5. The syringe assembly defined in claim 1, further comprising
   a clamp on the tube intermediate the ends thereof actuatable to restrict flow through the tube.

6. The syringe assembly defined in claim 1, further comprising
   a check valve in the tube oriented to prevent flow away from the syringe.

7. The syringe assembly defined in claim 1, further comprising:
   a three port valve in the tube having a lateral connection; and
   a second tube independent of the first-mentioned tube connected to the lateral connection of the valve.

8. The syringe assembly defined in claim 7, further comprising
   a flexible container connected to the second tube.

9. The syringe assembly defined in claim 1, further comprising:
   a tee connected in the tube intermediate the ends thereof and having a laterally open connection;
   a second tube independent of the first-mentioned tube having an inner end connected to the connection and an outer end; and
   a seal hermetically closing the outer end of the second tube.

10. The syringe assembly defined in claim 1, further comprising:
    a tee connected in the tube intermediate the ends thereof and having a laterally open connection;
    a second tube independent of the first-mentioned tube having an inner end connected to the connection and an outer end; and
    a flexible container connected to the outer end of the second tube.

11. The syringe assembly defined in claim 1 wherein the outlet and the inner end are formed as a luer connection and are provided with means for evidencing tampering therewith.

12. The syringe assembly defined in claim 1 wherein the tube is provided with identical identifying indicia at each of its ends.

13. A syringe assembly comprising:
    a plurality of syringes each having an outlet opening;
    a respective inner tubes each having an inner end hermetically sealed over the outlet opening of a respective one of the syringes and an outer end, whereby any contents of the syringe can flow unimpeded via the outlet into the respective tube and vice versa;
    a manifold having respective inlets hermetically sealed with the outer ends of the inner tubes and an outlet;
    a second tube formed of a thermoplastic synthetic resin and having an inner end hermetically sealed over the outlet and an outer end; and
    a seal unitarily formed with the tube and hermetically closing the outer end of the second tube.

* * * * *